United States Patent [19]

Bradley et al.

[11] 4,073,287
[45] Feb. 14, 1978

[54] URETHRAL PROFILOMETRY CATHETER

[75] Inventors: William E. Bradley; Geoffrey Steven Gates, both of Minneapolis, Minn.

[73] Assignee: American Medical Systems, Inc., St. Louis Park, Minn.

[21] Appl. No.: 674,061

[22] Filed: Apr. 5, 1976

[51] Int. Cl.² ............................................. A61B 5/10
[52] U.S. Cl. ................................. 128/2 R; 128/25; 128/2.05 D; 128/2.1 E; 128/2.1 M; 128/349 R; 128/404
[58] Field of Search ........... 128/2.1 E, 2.1 M, 2.06 E, 128/2 R, 2 S, 2 N, 2.05 D, 2.05 E, 348 R, 404, 407–409, 416, 417, 418, 419 P

[56] References Cited

U.S. PATENT DOCUMENTS

| 1,989,282 | 1/1935 | Kimble et al. | 128/416 |
| 3,480,003 | 11/1969 | Crites | 128/2.1 E X |
| 3,533,403 | 10/1970 | Woodson | 128/2.06 E |
| 3,606,881 | 9/1971 | Woodson | 128/2.06 E |
| 3,680,544 | 8/1972 | Shinnick et al. | 128/2 R |
| 3,920,003 | 11/1975 | Ash et al. | 128/2.1 E X |
| 3,995,623 | 12/1976 | Blake et al. | 128/2.06 E |

OTHER PUBLICATIONS

USCI Cardiovasular Electrodes, . . . Catheters, June 1974, pp. 1–12.

Primary Examiner—Robert W. Michell
Assistant Examiner—Lee S. Cohen
Attorney, Agent, or Firm—Williamson, Baines, Moore & Hansen

[57] ABSTRACT

A catheter for performing urethral profilometry, and a method of making same, are provided herein. The catheter preferably comprises an elongated tubular body portion provided with a plurality of circumferentially spaced apart orifices for discharging fluid and a pair of flushly mounted flexible electrodes for sensing urethral electrical signals. A pair of electrical conductors connected to the electrodes deliver urethral signals externally of the catheter.

A method disclosed herein for providing a catheter with flexible electrodes comprises the steps of mixing powdered silver with a medical grade adhesive and a solvent, and afterwards forming the electrodes in the desired shape. Evaporation of the solvent concurrently with curing of the adhesive yields a permanently affixed flexible electrode. A method of providing fluid discharge orifices disclosed herein comprises the steps of placing the catheter coaxially within a rigid tool having a plurality of predrilled orifices provided therein, soaking the catheter in xylene or the like, and then drilling the catheter through the predrilled orifices to form fluid discharge holes of constant predetermined diameter.

8 Claims, 8 Drawing Figures

U.S. Patent  Feb. 14, 1978  Sheet 1 of 2  4,073,287
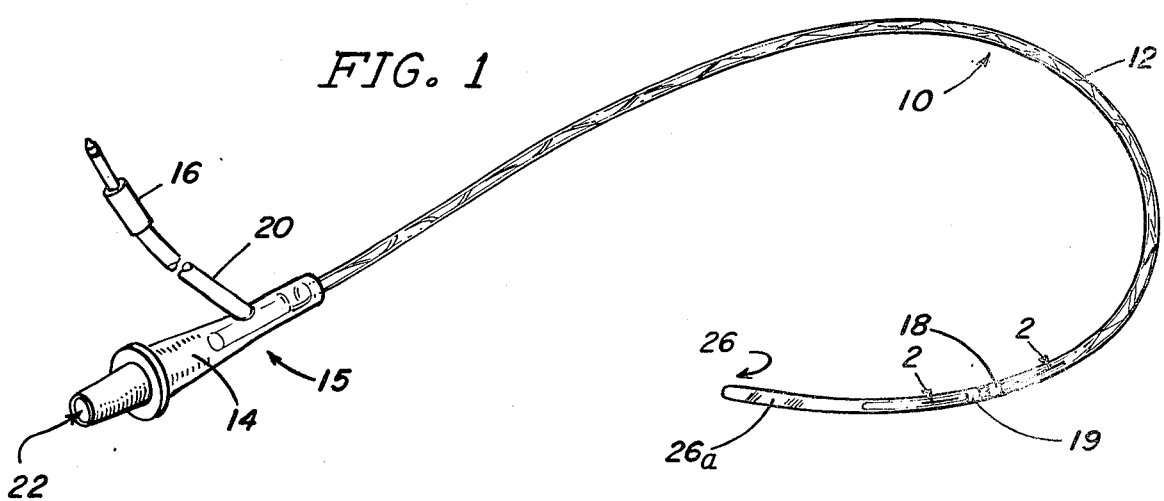
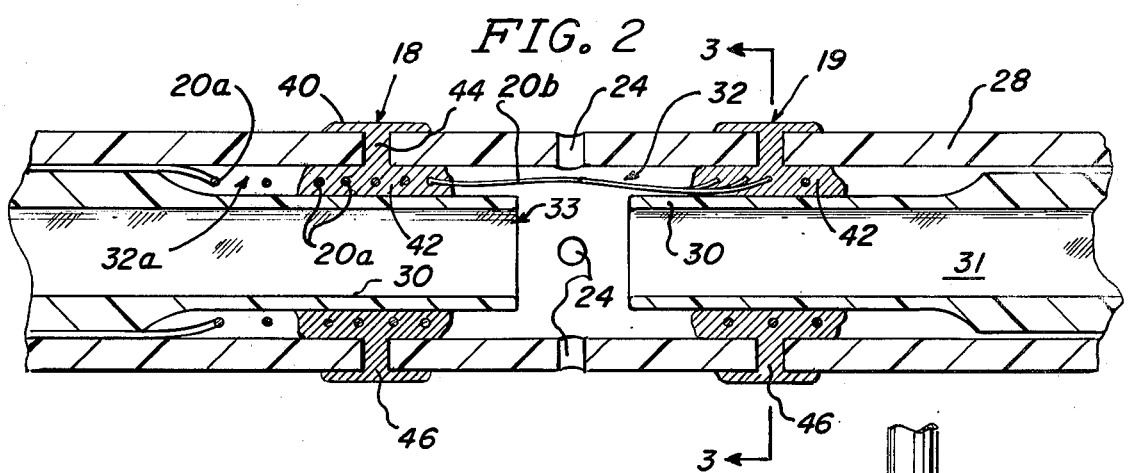
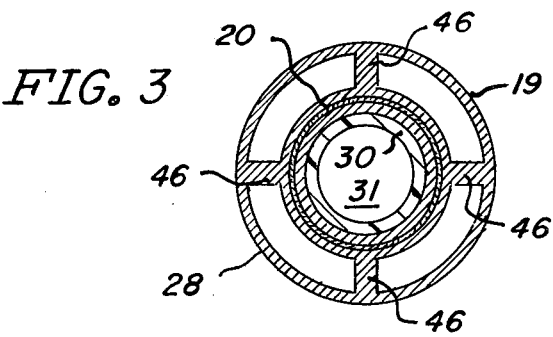
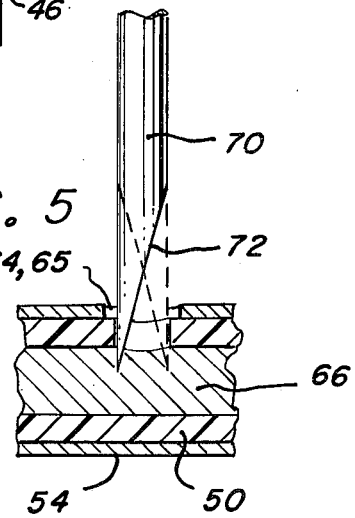
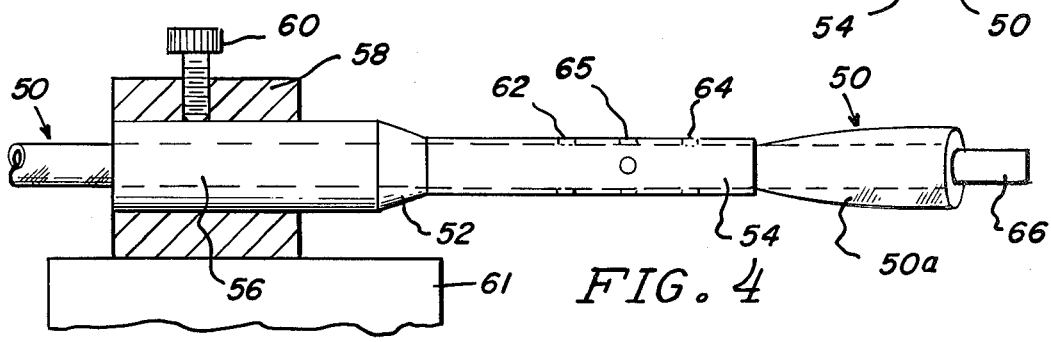

FIG. 6
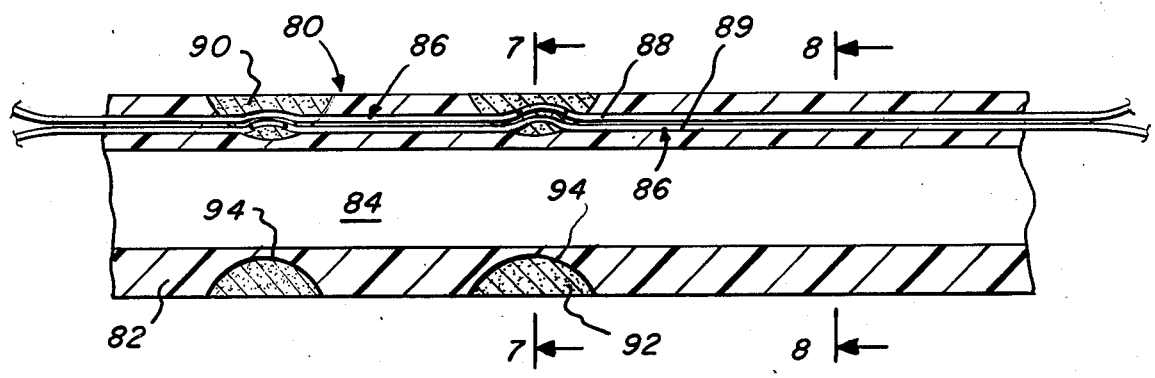
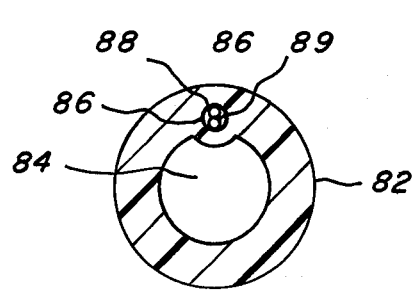
FIG. 8
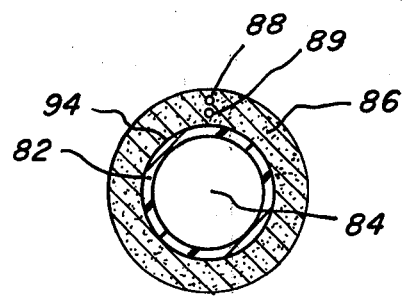
FIG. 7

URETHRAL PROFILOMETRY CATHETER

BACKGROUND OF THE INVENTION

This invention relates to urethral pressure profilometry. More particularly, the instant invention comprises a catheter and a method of making same which is adapted for use in profilometry and which will simultaneously derive electrical signals from the urethra.

Malfunction of the complex urinary tract can result in a variety of objectionable and unfortunate problems. One of the most common problems associated with urinary dysfunction is incontinence, or the inability to volitionally control micturition.

One diagnostic technique for investigating urinary difficulties is profilometry, involving the generation of a urethral pressure profile. The urethral pressure profile is a graphical record of pressure within the urethra at successive points along its length. It is known, for example, that continence will be maintained if the intraurethral pressure is greater than the intravesical pressure. Leakage of urine occurs when urethral pressure decreases to less than bladder pressure. The utility of the urethral pressure profile as a diagnostic technique is well known.

The generation of a urethral pressure profile involves the initial step of catheterizing a patient. The catheter must be connected to a source of fluid, such as carbon dioxide or water, and it must contain at least one discharge orifice for inputting fluid into the urethra. The input of fluid is maintained at a constant preset rate while fluid pressure is continuously monitored, and readings may be recorded on strip charts or the like. Fluid pressure varies directly with the resistance to flow, which, in turn, is due to the varying pressure exerted by the urethra covering the discharge orifices in the catheter. The urethral pressure profile will be derived as the catheter is withdrawn from the urethra. By displaying the results graphically, for example, a correlation of urethral pressure versus position within the urethra will be provided. The catheter is preferably withdrawn from the urethra at a constant velocity.

Catheters are generally comprised of soft rubber materials, such as latex or silicone rubbers. In the prior art it has been very difficult to accurately cut uniformly sized holes in silicone or latex materials because of the high elasticity and softness of same. Because of these characteristics the material will tend to give way or yield when a drill bit, for example, is applied, resulting in roughly formed holes of unpredictable diameter. In order to achieve quantitatively accurate results during profilometry, it is important to have fluid discharge orifices with smooth surfaces and uniform cross-sectional area, so that reproducible results are obtained with interchangeable catheters.

A prior art urethral catheter is shown in the U.S. Pat. No. 3,428,046, issued to Remer et al. on Feb. 18, 1969. An esophageal catheter is shown in U.S. Pat. No. 3,437,088, issued to L. Bielinski on Apr. 8, 1969. A multipurpose cathether on which a pair of electrodes are mounted is shown in U.S. Pat. No. 3,568,660, issued to N. Crites, Mar. 9, 1971. U.S. Pat. No. 3,815,611 shows a catheter on which a plurality of electrodes are mounted.

The hole drilling art as it relates to catheters is discussed in Urology, May 1975, Vol. V, No. 5.

Rigid catheter mounted electrodes for electromyography are shown in a copending application entitled "Method and Apparatus for Micturition Analysis," Ser. No. 566,044, filed Apr. 7, 1975, and owned by the same assignee as in this case. Interaction between rigid electrodes and the sensitive body tissues within the urethra normally causes objectionable patient pain as the catheter is slowly withdrawn from the urethra during generation of a urethral pressure profile. Even where significant pain is not produced with rigid electrodes, patient nervousness often results, yielding false or inaccurate diagnostic readings.

SUMMARY OF THE INVENTION

The present invention discloses a catheter for use with profilometry including flexible electrode portions for simultaneously measuring urethral electrical responses.

The catheter preferably comprises a tubular body portion having an input end adapted to be connected to a fluid source, a plurality of fluid output orifices disposed near a urethra-engaging end of the catheter body, and one or more flexible electrodes attached to the body portion for deriving urethral electrical signals. The electrodes are connected to conductors preferably extending longitudinally interiorally of the catheter, and which connect to suitable display apparatus for monitoring derived electrical signals. In the preferred embodiment the electrodes are formed from a mixture comprising powdered silver, medical grade adhesive, and a solvent such as xylene or the like. The mixture may be applied to the catheter in the desired form and location, and after the solvent evaporates a generally soft, adhered electrode will be permanently attached to the catheter. Because of its deformable characteristics, the electrode will not irritate or injure sensitive body tissues.

A method for providing constant diameter fluid discharge holes in a catheter disclosed herein comprises the steps of inserting a catheter coaxially through a tubular tool having a plurality of predefined holes formed therein, soaking the portion of the catheter in proximity of and including the tool in a dispersion agent solvent such as xylene, toluene or the like, and drilling the catheter through the predrilled orifices in the tool with a beveled hypodermic needle. When holes are drilled in this manner they will be of extremely uniform, consistent size and shape, and jagged irregularities associated with the prior art techniques will be omitted or avoided.

Thus an object of this invention is to provide a catheter suited for use with urethral profilometry.

An important object of this invention is to provide a catheter of the character described with at least one flexible electrode for deriving urethral electrical signals. It is a feature of this invention that, because of the flexible electrodes employed therewith, urethral electrical signals may be generated simultaneously with the generation of a urethral pressure profile without unnecessary pain or discomfort.

Another object of this invention is to provide a catheter with flushly mounted flexible electrodes.

Another object of this invention is to provide a catheter of the character described which is ideally adapted for deriving urethral electrical signals.

These and other objects of this invention, along with features of novelty appurtenant thereto, will appear or become apparent in the course of the following description.

BRIEF DESCRIPTION OF THE DRAWINGS

In the following drawings, which form a part of the specification and are to be construed in conjunction therewith, and in which like reference numerals have been employed to indicate like parts in the various views:

FIG. 1 is a perspective view of a catheter constructed in accordance with the teachings of this invention;

FIG. 2 is an enlarged longitudinal sectional view of the urethra-engaging end of the catheter shown in FIG. 1 disclosing the internal construction thereof;

FIG. 3 is a sectional view taken along line 3—3 in FIG. 2;

FIG. 4 pictorially depicts the relationship of certain tools employed in the formation of the fluid discharge orifices;

FIG. 5 is an enlarged, sectional view showing the hole drilling operation;

FIG. 6 is an enlarged longitudinal view of an alternative embodiment of a catheter, showing a portion thereof in section for clarity;

FIG. 7 is a sectional view taken along line 7—7 in FIG. 6; and

FIG. 8 is a sectional view taken along line 8—8 in FIG. 6.

DETAILED DESCRIPTION OF THE DRAWINGS

Referring now to the drawings, and more particularly to FIG. 1 thereof, a catheter 10 constructed in accordance with one embodiment of this invention is there shown. Catheter 10 preferably comprises an elongated flexible tubular body portion 12 which is adapted to be inserted into the urethra, an autoclavable connector 14 disposed at a fluid input end 15 of the catheter, and a connector plug 16 which is electrically connected to sensor electrodes 18 and 19 through conductor cable 20. The connector 14 is adapted to be connected to a source of fluid, such as carbon dioxide or the like, and fluid entering the catheter through an orifice 22 therein will be inputted interiorly of the urethra through a plurality of fluid discharge orifices 24 (FIG. 2), which are preferably positioned between the sensor electrodes 18 and 19. Electrodes 18 and 19 and fluid discharge orifices 24 are preferably positioned adjacent the urethra-entering end 26 of catheter 10. As best seen in FIG. 1, the urethra-engaging end 26 comprises a generally solid tip portion 26a, which facilitates installation of the apparatus.

Catheter 10 is preferably comprised of a physiologically inert, medical grade silicone elastomer sold under the tradename "Silastic," available from the Dow Corning Corporation, Midland, Michigan 48640. Body 12 preferably comprises an outer flexible tube 28 having an inner flexible tube 30 coaxially disposed therewithin. Fluid entering orifice 22 travels through the internal passageway 31 in tube 30. A slight space 32 defined between tubes 30 and 28 houses insulated conductor wires 20a and 20b, which may be spirally wound about tube 30 interiorly of body 12. It will be appreciated that the conductors 20a and 20b are electrically in contact with electrodes 18 and 19 respectively and extend rearwardly to plug 16, passing interiorly of external cable 20.

Fluid within tube 30 exits therefrom through an outlet portion 33 therein. Portion 33 is positioned immediately adjacent fluid output orifices 24 provided in outer tube 28. Thus fluid inputted into the catheter is dispensed outwardly of orifices 24. Each of the fluid discharge orifices 24 is substantially circular in profile and they are of uniform likeness in size and shape. Orifices 24 are provided at radially positioned intervals about the circumference of the catheter body. Flexible deformable electrodes 18 and 19 provide an internal fluid-tight seal, thereby preventing fluid from traveling backwards in the catheter within space 32a, for example. The solid portion 26a blocks lumen 31 distal to the orifices and seals space 32a distal to electrode 19.

Electrodes 18 and 19 comprise an outer band portion 40 which is adapted to electrically contact the urethral tissue, an inner band portion 42 disposed between adjacent walls of tubes 28 and 30, and a substantially vertically oriented portion 44 which integrally connects portions 40 and 42. It will be apparent that portion 44 penetrates electrode holes 46 provided within tube 28 through a method to be later described. The inner circular band portion 42 of each electrode makes electrical contact with conductors 20a or 20b which are stripped of insulation and wound about tube 30.

Each of the electrodes is preferably comprised of a mixture of electrically conductive, metallic powder, such as Mallinckrodt silver metal precipitated analytical reagent, and a silicone medical adhesive, such as Dow Corning Type A adhesive. The mixture is substantially soft in characteristic and yet results in a permanent attachment to the tubular walls of the catheter.

Formation of the electrode rings is facilitated by mixing the above mentioned mixture with a dispersion agent solvent, such as xylene, toluene, freon or other silicone solvent, resulting in a substantially liquid mixture. Consequently the electrodes may be formed in the desired size and shape. After the xylene (or other reagent solvent) evaporates and the adhesive cures, the electrodes will be permanently adhered to the catheter. In a preferred embodiment a relatively low ratio of adhesive to silver particles is employed, being between approximately 1:3 to 1:5 by weight. This low ratio of adhesive to silver increases electrical conductivity characteristics, and the even dispersion accounts for the strength of the silver silicone mixture.

The silver silicone adhesive mixture is preferably injected through the hole portions 46 in order to make electrical contact with the underlying conductors 20a and/or 20b. To form the electrode rings the adhesive is preferably wiped onto strips of tape having a predetermined width corresponding to the selected width of the electrodes. The tape is then wound around the catheter at the appropriate positions overlying electrode holes 46, with the adhesive side down. When the silver silicone adhesive dries, the tape may be lifted off the catheter, leaving smooth, electrically conductive rings. The combination of smoothness and softness of the electrically conductive surface material minimizes the possibility of trauma to the urethra during insertion and withdrawal.

Without special handling, holes in silicone tubing cannot be cut accurately. The high elasticity and softness of the silicone tubing allow the material to give way when pressure is applied by a drill bit or other cutting piece. The shifting of the material during cutting yields a rough hole of unpredictable diameter. The instant catheter is characterized by fluid discharge orifices 24 having substantially uniform sizes and shapes. Likewise, electrode orifices 46 are of similarly uniform consistency.

Referring now to FIGS. 4 and 5, apparatus for drilling holes in silicone tubing is there depicted. In FIG. 4 a flexible silicone tube 50 has been coaxially inserted within a generally tubular drilling tool 52. Tool 52 preferably has a first region 54 having an inner diameter substantially the same as the outer diameter of silicone tubing 50, and an integral larger diameter area 56 which is adapted to be held within a jib 58 via a setscrew 60. Jig 58 is held stationary on a lathe bed 61. Guide holes 62, 64 and 65 are located at radially positioned intervals along the circumference of tool portion 54 to facilitate the drilling operation. A generally cylindrical rod 66 may first be inserted coaxially within tube 50 to prevent deformation of the walls thereof. Rod 66 is preferably comprised of a low molecular weight polyethylene resin wax, available from Eastman Chemical Products under the tradename "Epolene," Type C-10.

Before the drilling operation is commenced, at least that portion of tube 50 within the jig and tool apparatus is soaked in xylene (or similar solvent) for approximately 15 to 20 minutes. As indicated in FIG. 4, this soaking will result in expanding of that portion 50a of the silicone tubing not confined within the tool 52. Restraint applied by the wax rod 66 and the tool 52 prevent the Silastic tubing from expanding significantly in this region. As a result of the soaking, the silicone tubing absorbs the xylene (or other solvent) and the internal strain within the tubing weakens the material.

After tube 50 is soaked in an appropriate solvent, the drilling operation illustrated in FIG. 5 may commence. The cutting tool is preferably a hypodermic needle 70 having a typical beveled portion 72 thereof. The rotating hypodermic needle is inserted through an orifice 64, for example, into cutting engagement with the tube 50 confined between rod 66 and tool portion 54. In this manner holes having substantially uniform sizes and shapes will be produced, thereby facilitating construction of the electrodes and operation of the fluid discharge orifices. Since each of the fluid discharge orifices 24 will be evenly spaced apart and will be uniform in constructional size and shape, the fluid outputted by the catheter into the urethra will be generarlly evenly distributed, facilitating quantitative urethral pressure profilometry.

An alternative embodiment of this invention is shown in FIG. 6. Catheter 80 comprises an elongated, flexible tubular body portion 82 which includes a tubular passageway 84 therewithin for distribution of gas or fluid in the previously described manner. A smaller lumen portion 86 is molded within the wall of the flexible tubular body 82 to provide a space for conductor wires 88 and 89. It should be understood that the electrode wires 88 and 89 extend longitudinally along the length of the catheter and are connected to the electrodes 90 and 92 in a manner which will be later described.

Each of the electrodes 90 and 92 is flushly mounted to the catheter body by applying the previously described metallic solvent mixture within a recessed area provided on the catheter surface. For example, the recessed indentation 94 provides an indented seat into which the electrode may be formed. The recess 94 is actually in the form of a groove which is extended around the entire circumference of the catheter. Alternatively, the electrodes could be placed in configurations of alternative sizes and shapes. In the preferred embodiment the indentation 94 is formed by grinding the catheter body with a high-speed abrasive wheel. The catheter stock employed is preferably an all-silicone catheter sold under the tradename "Dover," and available from TEK Products, 3109 Mount Pleasant Street, Racine, Wis. 53404.

As mentioned, the conductor electrodes 88 and 89 extend longitudinally down the body of the catheter and are housed within the small lumen 86. It will be apparent that the catheter electrodes extend into and through the small lumen 86. The short segment of wire 88 disposed within electrode 92 is stripped of its insulation in this area so that when the electrode is deposited in the manner previously described, electrical contact between the silver particles adhering to the silicone body of the catheter and the stripped preferably copper wire 89 will be made. The electrode conductor wires 88 and 89 thus extend longitudinally through the electrodes and do not need to be wrapped around the body of the catheter in this embodiment. Note that conductor 89 is insulated within electrode 92 and thus electrically isolated therefrom. Conductor 89 is electrically in contact with electrode 90, while conductor 88 is insulated therefrom.

Because of the small size of the electrode wire lumen 86, it can be very difficult to pass the conductor wires down the length of the catheter during the assembly of the apparatus. In order to remedy this problem, the catheter is first soaked with xylene, toluene, freon, or other hydrocarbon solvents, thereby greatly expanding the catheter in volume. After soaking in the solvent the size of lumen 86 will become greatly increased so that the wires 88 and 89 can be pulled into position therethrough. As a result of soaking in the solvent the slickness of the silicone body of the catheter increases. The combination of increased hole size and reduced friction characteristics allows the technician to advance a heavy strand of preferably nylon fishline or prolene suture (size zero) to the entire length of the electrode wire lumen 86. After tying the electrode wires can then be pulled into place through the smaller lumen 86. After the solvent is driven off quickly through heated forced air, for example, the silicone catheter will contract, thereby retaining its original size and strength. Since the electrode conductor wires are housed within the small lumen molded into the catheter wall, they will be protected from corrosion by body fluids. Furthermore, since there is no connection between the electrode lumen and the main lumen, no recess exists that can trap body fluids which could cause problems when the catheter is reused.

From the foregoing, it will be seen that this invention is one well adapted to obtain all the ends and objects herein set forth, together with other advantages which are obvious and which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A catheter for performing urethral profilometry comprising:
   an elongated tubular body portion for insertion into the urethra, said body portion having an urethra engaging end and a fluid input end and comprising a first flexible tube and a second flexible tube coaxially disposed internally of said first tube;

at least one fluid output orifice disposed adjacent said urethra engaging end of said body portion and in fluid flow communication with said fluid input end;

an elongated conductor passage defined between said first and second flexible tubes and extending parallel to the longitudinal axis of said tubes;

conductor means disposed in said elongated conductor passage for delivering electrical signals externally of said catheter;

at least one electrode hole extending through said first flexible tube of said body portion; and electrode means attached to said body portion for sensing electrical signals, said electrode means comprising an outer circular band portion overlying said first flexible tube for sensing electrical activity, an inner circular band portion disposed below said electrode hole between said first and second flexible tubes in electrical contact with said conductor means, and an integral portion thereof extending through said electrode hole between said inner and outer band portions.

2. The catheter as defined in claim 1 wherein said electrode means is flexible and comprises an electrically conductive metallic powder mixed with an adhesive.

3. The catheter as defined in claim 1 wherein said urethra-engaging end comprises a solid tip portion integrally connected to said first flexible tube.

4. The catheter as defined in claim 1 wherein said fluid input end comprises an autoclavable connector adapted to be attached to a source of fluid.

5. The combination as in claim 1 wherein said electrode means comprises first and second flexible ring shaped electrodes spaced apart from each other a predetermined distance on said body portion, and a plurality of fluid output orifices are radially disposed about the circumference of said body portion between said first and second ring-shaped electrodes.

6. The combination as in claim 5 wherein said flexible electrode rings each comprise an electrically conductive metallic powder mixed with an adhesive.

7. The catheter as defined in claim 1 wherein:

said fluid output orifice extends through said first flexible tube;

fluid inlet means connected to said fluid input end of said tubular body portion;

said second flexible tube is connected to said fluid inlet means at said fluid input end of said tubular body portion and has an outlet end in fluid flow communication with said fluid output orifice; and said inner circular band portion of said electrode means is in tight, sealing contact with said first and second flexible tubes and thereby prevents fluid backflow through said conductor passage.

8. A catheter for performing medical diagnosis such as urethral profilometry, said catheter comprising:

an elongated tubular body portion for insertion into the urethra, said body portion having an urethra engaging end and a fluid input end;

at least one fluid output orifice disposed adjacent said urethra engaging end and in fluid flow communication with said fluid input end;

a conductor passage extending longitudinally within the walls of said tubular body portion;

conductor wire means disposed within said conductor passage for delivering electrical signals externally of said catheter;

a groove recess extending around the circumference of said tubular body portion on the outside surface thereof and extending into said conductor passage;

electrode means attached to said body portion for sensing electrical signals, said electrode means comprising a flexible electrode ring disposed in its entirety within said recess with its outer surface flush with the outside surface of said tubular body portion, and said electrode ring being comprised of an electrically conductive metallic powder mixed with an adhesive applied in a flowable state and bonded to said tubular body portion within said recess; and an electrically conductive portion of said conductor wire means embedded in said flexible electrode ring in electrical contact therewith within said recess.

* * * * *